US008826727B2

(12) United States Patent
Kato et al.

(10) Patent No.: US 8,826,727 B2
(45) Date of Patent: Sep. 9, 2014

(54) GAS SENSOR

(75) Inventors: Kenji Kato, Nagoya (JP); Kohei Ito, Komaki (JP)

(73) Assignee: NGK Spark Plug Co., Ltd., Aichi (JP)

(*) Notice: Subject to any disclaimer, the term of this patent is extended or adjusted under 35 U.S.C. 154(b) by 37 days.

(21) Appl. No.: 13/336,454

(22) Filed: Dec. 23, 2011

(65) Prior Publication Data

US 2012/0160012 A1 Jun. 28, 2012

(30) Foreign Application Priority Data

Dec. 27, 2010 (JP) ................................ 2010-289465

(51) Int. Cl.
*G01N 7/00* (2006.01)
*G01N 27/419* (2006.01)

(52) U.S. Cl.
CPC .................................. *G01N 27/419* (2013.01)
USPC ....... 73/31.05; 73/23.31; 204/424; 205/783.5

(58) Field of Classification Search
USPC .............. 73/23.1, 31.01, 31.03, 31.05, 31.07; 204/410–412, 424–426; 205/781, 784, 205/788
See application file for complete search history.

(56) References Cited

U.S. PATENT DOCUMENTS

| | | | | |
|---|---|---|---|---|
| 6,045,673 A * | 4/2000 | Kato et al. | ..................... | 204/425 |
| 6,533,911 B1 * | 3/2003 | Fujita et al. | ..................... | 204/424 |
| 6,695,964 B1 * | 2/2004 | Ando et al. | ..................... | 205/781 |
| 7,321,287 B2 * | 1/2008 | Ota et al. | ........................ | 338/25 |
| 8,012,325 B2 * | 9/2011 | Oya et al. | ....................... | 204/429 |
| 8,382,973 B2 * | 2/2013 | Sugaya et al. | ................ | 205/781 |
| 2006/0255902 A1 | 11/2006 | Ota et al. | | |
| 2009/0242401 A1 * | 10/2009 | Horisaka et al. | ............. | 204/412 |

FOREIGN PATENT DOCUMENTS

| | | |
|---|---|---|
| EP | 0 791 827 A1 | 8/1997 |
| EP | 1722219 A1 | 11/2006 |
| EP | 2107365 A2 | 10/2009 |
| JP | 9-288084 A | 11/1997 |
| JP | 9-297119 A | 11/1997 |
| JP | 11-311613 A | 11/1999 |

OTHER PUBLICATIONS

Kato et al., Thick Film ZrO2 NOx Sensor, NGK Insulators. Ltd.—Society of Automotive Engineers, Inc. 1996.*
Nobuhide Kato, et al.; "Thick Film $ZRO_2$ $NO_x$ Sensor"; SAE Technical Paper Series 960334; Reprinted from: Electronic Engine Controls 1996 (SP-1149); Copyright 1996 Society of Automotive Engineers, Inc.; International Congress & Exposition, Detroit, Michigan, Feb. 26-29, 1996.
Japanese Office Action mailed on Mar. 19, 2013 from the Japanese Patent Office in Japanese Application No. 2011-032651.

* cited by examiner

*Primary Examiner* — Hezron E Williams
*Assistant Examiner* — Hoang Nguyen
(74) *Attorney, Agent, or Firm* — Sughrue Mion, PLLC

(57) ABSTRACT

A gas sensor including a reduction section (18) for reducing $NO_2$ contained in exhaust gas to NO. The reduction section (18) is provided on the upstream side of a first diffusion resistor section (103) which limits the flow of the exhaust gas into a first measurement chamber (101). When $NO_X$ passes through the first diffusion resistor section (103), $NO_2$ which has a greater molecular weight than NO has a lower degree of diffusion. Since $NO_2$ is reduced to NO at the reduction section (18), the exhaust gas passing through the first diffusion resistor section (103) hardly contains $NO_2$. Therefore, the speed of flow of $NO_X$ through the first diffusion resistor section (103) is not limited by $NO_2$, whereby sensitivity for detection of $NO_X$ can be improved.

3 Claims, 2 Drawing Sheets

GAS SENSOR

TECHNICAL FIELD

The present invention relates to a gas sensor including a detection element for detecting the concentration of $NO_X$ contained in a gas to be detected (hereinafter referred to as "object gas").

BACKGROUND ART

There has been known a gas sensor which is provided in an exhaust passage of an internal combustion engine such as an automotive engine and which includes a detection element whose output changes with the concentration of a specific gas (oxygen, $NO_X$, etc.) contained in exhaust gas. For example, the detection element of an $NO_X$ sensor capable of detecting the concentration of $NO_X$ has a layered structure including at least one cell composed of a solid electrolyte member and a pair of electrodes provided thereon. The detection element includes a first measurement chamber (first internal cavity) into which exhaust gas is introduced via a diffusion resistor section (first diffusion path); and a second measurement chamber (second internal cavity) into which exhaust gas whose oxygen has been pumped out in the first measurement chamber is introduced (for example, see Non-patent Document 1).

Oxygen contained in the exhaust gas introduced into the first measurement chamber is pumped out to the outside by the cell, whereby the concentration of oxygen remaining in the exhaust gas introduced into the second measurement chamber is adjusted to a predetermined low level. $NO_X$ contained in exhaust gas includes NO and $NO_2$. According to Non-patent Document 1, most of $NO_2$ is reduced to NO in the first measurement chamber. In the second measurement chamber, NO is decomposed to nitrogen and oxygen by the catalytic action of an electrode formed of noble metal such as Pt or Rh. At that time, oxygen derived from the decomposed NO (oxygen having constituted NO or $NO_2$ ($NO_X$)) is pumped out by the cell. In the cell, electrons conveyed via oxygen ions are detected in the form of current. The oxygen concentration detected in this manner is offset by the concentration of the residual oxygen (the above-mentioned adjusted oxygen concentration), whereby the concentration of $NO_X$-originating oxygen (ultimately, the concentration of $NO_X$) is detected.

PRIOR ART DOCUMENT

Non-Patent Document

[Non-patent Document 1] N. Kato et al., "Thick Film ZrO2 $NO_X$ Sensor", SAE Technical paper series 960334 (1996)

SUMMARY OF THE INVENTION

Problem to be Solved by the Invention

However, according to Non-patent Document 1, there has been known that the sensitivity of such a detection element to $NO_2$ is lower than that to NO, and is about 80% the sensitivity to NO. Therefore, improving the sensitivity to $NO_2$ (thus, improving the sensitivity to $NO_X$) has been demanded. Notably, according to Non-patent Document 1, conceivably, the difference in sensitivity occurs because of a chemical reaction of reducing $NO_2$ to NO occurs in the first measurement chamber as described above, and $NO_2$ is low in the degree of diffusion (that is, the speed at which $NO_2$ passes through a diffusion resistor section is low) as compared with NO.

The present invention has been accomplished in order to solve the above-described problem, and its object is to provide a gas sensor which can improve sensitivity to $NO_X$.

Means for Solving the Problems

According to a mode of the present invention, there is provided a gas sensor for detecting concentration of $NO_X$ contained in an object gas, comprising a first measurement chamber into which the object gas is introduced via a diffusion resistor section which limits flow of the object gas therethrough; a reduction section provided upstream of the diffusion resistor section and reducing $NO_2$ contained in the object gas introduced into the first measurement chamber to NO; a first oxygen pump cell having a first solid electrolyte layer and a pair of first electrodes provided on the inner and outer sides of the first measurement chamber; a second measurement chamber which is located downstream of the first measurement chamber and into which the object gas is introduced from the first measurement chamber; and a second oxygen pump cell having a second solid electrolyte layer and a pair of second electrodes provided on the inner and outer sides of the second measurement chamber, wherein a current corresponding to the amount of oxygen produced as a result of decomposition of NO contained in the object gas introduced into the second measurement chamber flows between the pair of second electrodes.

$NO_2$ contained in the object gas is more likely to receive the flow resistance of the diffusion resistor section (is lower in passing speed), as compared with NO. However, the reduction section provided on the upstream side of the diffusion resistor section enables $NO_2$ to pass through the diffusion resistor section after being reduced to NO. That is, since the speed at which $NO_2$ passes through the diffusion resistor section when the object gas is introduced into the first measurement chamber does not become a limiting factor for detection of the $NO_X$ concentration, the sensitivity of the gas sensor can be enhanced.

In the mode of the present invention, a heater for heating the reduction section may be provided. In this case, as a result of heating by the heater, the reduction section heats the object gas flowing through the reduction section to at least a reduction temperature required for reduction of $NO_2$ to NO. Since, as a result of heating of the reduction section by the heater, $NO_2$ contained in the object gas is heated to at least the reduction temperature when $NO_2$ passes through the reduction section, the reduction of $NO_2$ to NO can be performed more reliably at the reduction section, whereby the sensitivity of the gas sensor can be enhanced more reliably.

In the mode of the present invention, the reduction section may bear a reduction catalyst which catalyzes a reduction reaction of $NO_2$ to NO. In this case, since the reduction reaction of $NO_2$ to NO is accelerated by the reduction catalyst, the reduction of $NO_2$ to NO can be performed further reliably at the reduction section, whereby the sensitivity of the gas sensor can be enhanced further reliably.

In the mode of the present invention, each of the diffusion resistor section and the reduction section may be is formed of a porous body having a large number of continuous pores through which the object gas flows. In this case, the reduction section may have a porosity higher than that of the diffusion resistor section. In the case where the reduction section is formed of a porous body, the reduction section has high heat accumulation performance, whereby the reduction of $NO_2$ contained in the object gas passing through the reduction section to NO can be accelerated. Also, in the case where the porosity of the reduction section is higher than that of the diffusion resistor section, the reduction section hardly produces a flow resistance against $NO_2$ before being reduced to NO. Therefore, the detection of the $NO_X$ concentration is not limited in speed through provision of the reduction section, whereby the sensitivity of the gas sensor can be secured.

MODE FOR CARRYING OUT THE INVENTION

Figure 1:
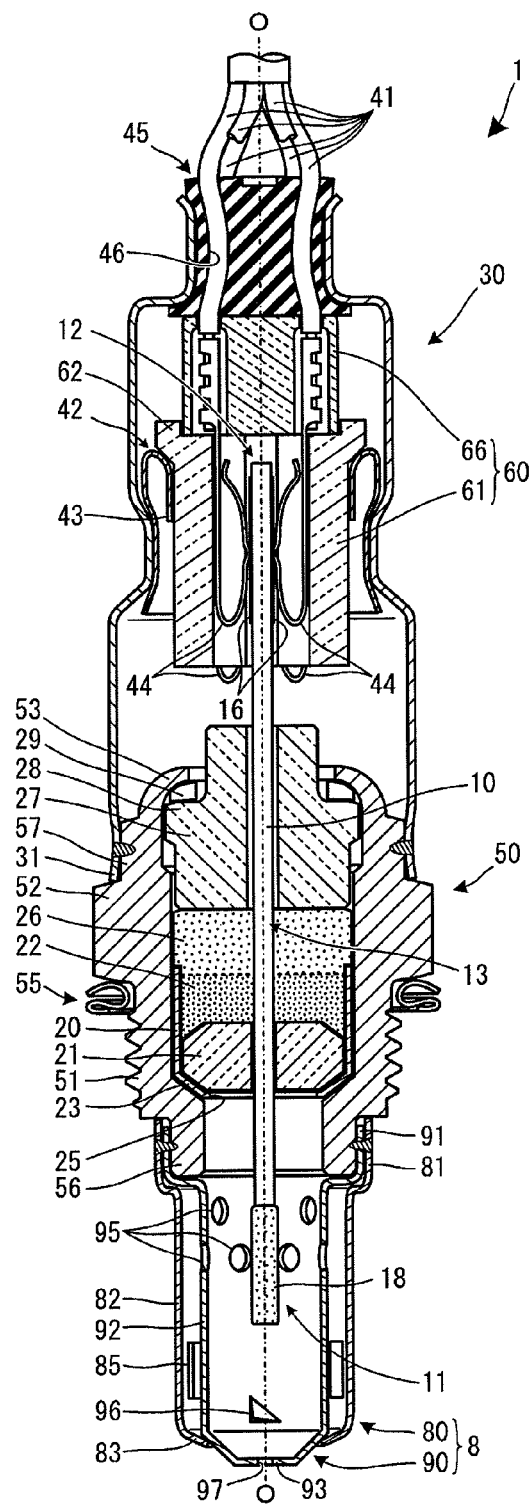
FIG. 1 Sectional view of an $NO_X$ sensor 1.

A gas sensor according to an embodiment of the present invention will next be described with reference to the drawings. First, the structure of an $NO_X$ sensor 1 will be described, by way of example, with reference to FIG. 1. In FIG. 1, the direction of an axis O (represented by a dash-dot line) of the $NO_X$ sensor 1 coincides with the vertical direction. In the following description, a side toward a front end portion 11 of a detection element 10 held in the $NO_X$ sensor 1 is referred to as a front end side of the $NO_X$ sensor 1, and a side toward a rear end portion 12 thereof is referred to as a rear end side of the $NO_X$ sensor 1.

The $NO_X$ sensor 1 shown in FIG. 1 is attached to an exhaust pipe (not shown) of an automobile. The front end portion 11 of the detection element 10 held in the $NO_X$ sensor 1 is exposed to exhaust gas which flows through the exhaust pipe, for detecting the concentration of $NO_X$ contained in the exhaust gas. The detection element 10 assumes the form of a plate of narrow width extending in the direction of the axis O. The detection element 10 is a substantially rectangular columnar laminate in which a gas detection section 14 (see FIG. 2) for detecting the concentration of $NO_X$, and a heater section 15 (see FIG. 2) for promptly activating the gas detection section 14 through application of heat are stacked on each other. Notably, in FIG. 1, the plate thickness direction of the detection element 10 corresponds to the left-right direction of the sheet, and the plate width direction thereof corresponds to the front-back direction of the sheet (direction perpendicular to the sheet). Notably, the structure of the detection element 10 will be described in detail later. Also, a portion for detecting the concentration of $NO_X$ is provided within the front end portion 11 of the detection element 10, and a reduction section 18, which will be described later, is provided on the circumference of the front end portion 11. Six electrode pads 16 (FIG. 1 shows two of them) are formed on the rear end portion 12 of the detection element 10 for electrically connecting the detection element 10 and an external circuit (not shown).

A closed-bottomed tubular metal cup 20 is disposed slightly frontward of the axial center of a trunk portion 13 of the detection element 10, and has an opening 25 formed in the bottom wall thereof. The detection element 10 is inserted through the interior of the metal cup 20 such that the front end portion 11 projects frontward from the opening 25. The metal cup 20 is a member for holding the detection element 10 in a metallic shell 50. A front-end peripheral-portion 23 located at a peripheral portion of the bottom wall of the metal cup 20 is tapered toward a circumferential wall portion of the metal cup 20. A ceramic ring 21 made of alumina and a talc ring 22 formed by compacting a talc powder are disposed within the metal cup 20 such that they are laminated in the direction of the axis O, and surround the circumference of the detection element 10. The talc ring 22 is crushed within the metal cup 20 so as to tightly fill an associated space, thereby holding the detection element 10 in position in the metal cup 20.

An assembly of the metal cup 20 and the detection element 10 is surrounded by and held by the tubular metallic shell 50. The metallic shell 50 is adapted to fixedly attach the $NO_X$ sensor 1 to the exhaust pipe (not show) of an automobile. The metallic shell 50 has a mounting portion 51 which is formed on an outer circumferential surface of the metallic shell 50 and located on a side toward the front end of the metallic shell 50. The mounting portion 51 has an external thread formed thereon for attachment to the exhaust pipe. The metallic shell 50 has a front-end engagement portion 56 which is located frontward of the mounting portion 51 and with which a protector 8 to be described later is engaged. The metallic shell 50 also has a tool engagement portion 52 which is formed at an axially central portion of the outer circumferential surface of the metallic shell 50 and with which a mounting tool is engaged. The metallic shell 50 further has a rear-end engagement portion 57 which is located rearward of the tool engagement portion 52 and with which a sheath 30 to be described later is engaged, and a crimp portion 53 which is located rearward of the rear-end engagement portion 57 and adapted to crimp-hold the detection element 10 in the metallic shell 50. In order to prevent leakage of gas when the $NO_X$ sensor 1 is attached to the exhaust pipe, an annular gasket 55 is fitted to a portion of the metallic shell 50 between the tool engagement portion 52 and the mounting portion 51.

The metallic shell 50 has a stepped portion on its inner circumferential surface at a position near the mounting portion 51. The front-end peripheral-portion 23 of the metal cup 20, which holds the above-described detection element 10, is engaged with the stepped portion. Furthermore, a talc ring 26 is placed into the metallic shell 50 along the inner circumference of the metallic shell 50 toward the rear end of the metal cup 20 in such a state that the detection element 10 is inserted through the talc ring 26. A tubular sleeve 27 is fitted into the metallic shell 50 such that the sleeve 27 presses the talc ring 26 from the rear end side of the talc ring 26 and the detection element 10 extends through the sleeve 27. The sleeve 27 has a step-like shoulder portion 28 formed on the outer circumferential surface of a rear end portion of the sleeve 27. An annular packing 29 is disposed on the shoulder portion 28. In this condition, the crimp portion 53 of the metallic shell 50 is crimped radially inward, and the crimp portion 53 presses the shoulder portion 28 of the sleeve 27 frontward via the packing 29. As a result of this crimping, the talc ring 26, which is pressed by the sleeve 27, is crushed within the metallic shell 50, thereby tightly filling an associated space. By means of the talc ring 26 and the talc ring 22, which is previously placed in the metal cup 20, the metal cup 20 and the detection element 10 are held in position in the metallic shell 50.

The front-end engagement portion 56 of the metallic shell 50 is formed into a tubular shape, and the protector 8 is fitted thereon. The protector 8 surrounds the circumference of the front end portion 11 of the detection element 10 to thereby protect the detection element 10 from water, breakage caused by physical impact, etc. The protector 8 is fixed to the front-end engagement portion 56 by means of resistance welding or laser welding. The protector 8 has a double structure; i.e., is composed of a bottomed tubular inner protector 90 and a tubular outer protector 80 which circumferentially surrounds the inner protector 90 while forming a clearance between the inner circumferential surface of the outer protector 80 and the outer circumferential surface of the inner protector 90.

The inner protector 90 has a plurality of inner introduction holes 95 formed in a rear end portion of a circumferential wall 92 thereof, a plurality of drain holes 96 formed in a front end portion of the circumferential wall 92, and a discharge opening 97 formed in a bottom wall 93 thereof. A base end portion 91 of the inner protector 90 located on the side toward the open end thereof (the rear end side) is engaged with the outer circumference of the front-end engagement portion 56. The outer protector 80 includes a plurality of outer introduction holes 85 formed in a front end portion of a circumferential wall 82 thereof. A base end portion 81 of the outer protector 80 located on the side toward the open end thereof is engaged with the outer circumference of the base end portion 91 of the inner protector 90. In this state, laser welding is performed on the outer circumference of the base end portion 81, whereby the base end portion 81 is joined to the front-end engagement portion 56 of the metallic shell 50, along with the base end portion 91 of the inner protector 90. Thus, the outer protector 80 and the inner protector 90 are fixed to the metallic shell 50. Moreover, a front end portion 83 of the outer protector 80 is bent inward toward the circumferential wall 92 of the inner protector 90 so as to close the clearance between the outer protector 80 and the inner protector 90.

Meanwhile, the rear end portion 12 of the detection element 10 held by the metallic shell 50 projects rearward beyond the rear end (crimp portion 53) of the metallic shell 50. The rear end portion 12 is covered with a tubular separator 60 formed from an electrically insulating ceramic (in the present embodiment, alumina). The separator 60 is composed of a front separator 61 and a rear separator 66. The rear separator 66 is in engagement with a flange portion 62 of the front separator 61, which portion projects radially outward from the front separator 61. The front separator 61 accommodates connection portions (connection points) between the six electrode pads 16 formed on the rear end portion 12 of the detection element 10 and the six connection terminals (metallic terminals) 44 (FIG. 1 shows four of them) electrically connected to the corresponding electrode pads 16. In other words, electrical connection between the connection terminals 44 and the electrode pads 16 is established inside the front separator 61. The rear separator 66 accommodates connection portions between the connection terminals 44 and six lead wires 41 extending to the outside of the $NO_X$ sensor 1.

The tubular metal sheath 30 is disposed in such a manner as to surround the rear end portion 12 of the detection element 10 to which the separator 60 is fitted. A front open end 31 of the sheath 30 is engaged with the outer circumference of the rear-end engagement portion 57 of the metallic shell 50. The open end 31 is crimped radially inward, and laser welding is performed on the open end 31 along the entire outer circumference of the open end 31, whereby the open end 31 is joined to the rear-end engagement portion 57. The sheath 30 and the metallic shell 50 are thus fixedly united together.

A tubular metal holder 42 is disposed in the gap between the sheath 30 and the front separator 61. The metal holder 42 has a support portion 43, which is formed by inwardly bending a rear end of the metal holder 42. The front separator 61 is inserted through the metal holder 42 such that the flange portion 62 of the front separator 61 is engaged with the support portion 43, whereby the front separator 61 is supported by the metal holder 42. In this condition, a portion of the sheath 30 where the metal holder 42 is disposed is crimped radially inward, whereby the metal holder 42, which supports the front separator 61, is fixed to the sheath 30.

Next, a grommet 45 of fluorine-containing rubber is fitted into a rear end opening of the sheath 30, whereby the interior of the sheath 30 is sealed. The grommet 45 has six insertion holes 46 (FIG. 1 shows two of them). The above-mentioned six lead wires 41 extending from the separator 60 extend through the respective insertion holes 46. In this condition, while the grommet 45 presses the rear separator 66 against the front separator 61, the sheath 30 is crimped radially inward, whereby the grommet 45 is fixed to the rear end of the sheath 30.

Figure 2:
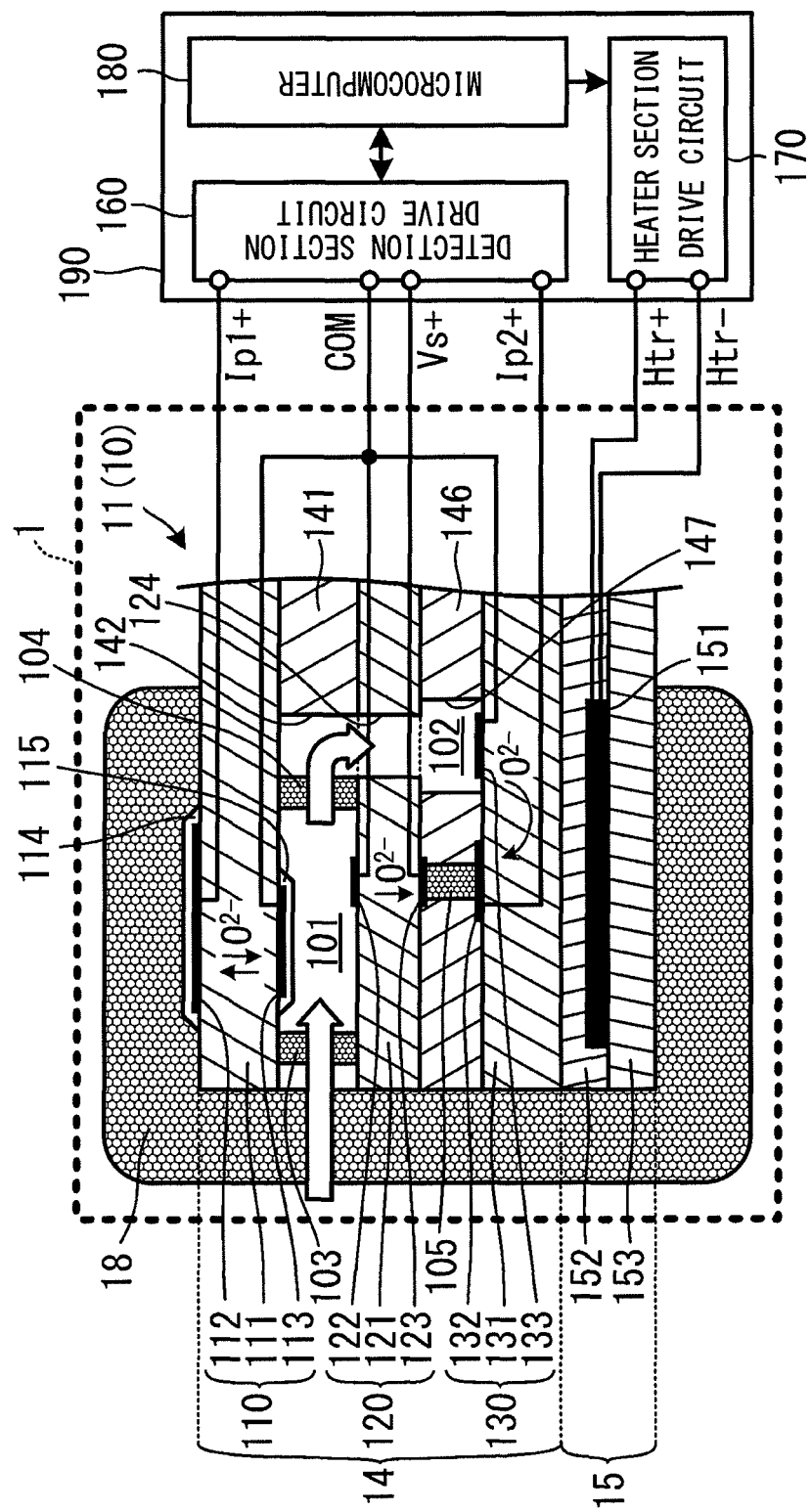
FIG. 2 Sectional view of a front end portion 11 of a detection element 10 connected to a sensor control apparatus 190.

Next, the structure of the detection element 10 will be described with reference to FIG. 2. In FIG. 2, which shows the front end portion 11 of the detection element 10, the left side of the sheet corresponds to the front end side of the detection element 10. Also, for description of operation, which will be provided later, FIG. 2 shows a state in which the $NO_X$ sensor 1 is connected to the sensor control apparatus 190 for controlling the drive of the detection element 10. The sensor control apparatus 190 includes a known microcomputer 180, which controls a detection section drive circuit 160 and a heater section drive circuit 170, which generate respective currents for driving the gas detection section 14 and the heater section 15. Since the configuration and operation of the sensor control apparatus 190 are known, in the following description, their descriptions will be omitted or simplified.

First, the structure of the gas detection section 14 of the detection element 10 will be described. As shown in FIG. 2, the gas detection section 14 has a layered structure in which three platelike solid electrolyte members 111, 121, and 131, and two insulators 141 and 146 formed of alumina or the like are alternately stacked. The gas detection section 14 has a first measurement chamber 101, a second measurement chamber 102, a reference oxygen chamber 105, a first oxygen pump cell 110, an oxygen partial pressure detection cell 120, and a second oxygen pump cell 130. In the following description, the first oxygen pump cell 110, the oxygen partial pressure detection cell 120, and the second oxygen pump cell 130 will be referred to as the Ip1 cell 110, the Vs cell 120, and the Ip2 cell 130, respectively.

The first measurement chamber 101 is a small space within the gas detection section 14 into which exhaust gas within an exhaust pipe (not shown) is first introduced. The first measurement chamber 101 is formed between the solid electrolyte member 111 and the solid electrolyte member 121. Electrodes 113 and 122 are disposed in the first measurement chamber 101 to be located on the solid electrolyte member 111 and the solid electrolyte member 121, respectively.

A first diffusion resistor section 103, which is a porous body formed of a ceramic material such as alumina and having a plurality of continuous pores, is provided in the first measurement chamber 101 to be located at the front end of the gas detection section 14. The first diffusion resistor section 103 functions as a partition between the exterior and interior of the first measurement chamber 101, and limits the amount per unit time of flow of the exhaust gas into the first measurement chamber 101. Similarly, a second diffusion resistor section 104, which is a porous body formed of a ceramic material such as alumina and having a plurality of continuous pores, is provided in the first measurement chamber 101 to be located on the side toward the rear end of the gas detection section 14. The second diffusion resistor section 104 functions as a partition between the first measurement chamber 101 and the second measurement chamber 102, and limits the amount per unit time of flow of the exhaust gas from the first measurement chamber 101 into the second measurement chamber 102.

The second measurement chamber 102 is a small space surrounded by the solid electrolyte member 111, the second diffusion resistor section 104, the wall surface of an opening 142 of the insulator 141, the wall surface of an opening 124 of the solid electrolyte member 121, the wall surface of an opening 147 of the insulator 146, and the solid electrolyte member 131. The second measurement chamber 102 communicates with the first measurement chamber 101 via the second diffusion resistor section 104. The exhaust gas whose oxygen concentration has been adjusted by the Ip1 cell 110 is introduced into the second measurement chamber 102. An electrode 133 is disposed on the upper surface of the solid electrolyte member 131 exposed to the second measurement chamber 102.

The reference oxygen chamber 105 is a small space which is surrounded by the wall surface of an opening provided in the insulator 146 independently of the second measurement chamber 102, the solid electrolyte member 121, and the solid electrolyte member 131. In the reference oxygen chamber 105, an electrode 123 is disposed on the surface of the solid electrolyte member 121, and an electrode 132 is disposed on the surface of the solid electrolyte member 131. A porous body formed of a ceramic material fills the reference oxygen chamber 105.

The Ip1 cell 110 includes the solid electrolyte member 111, and a pair of porous electrodes 112 and 113. The solid electrolyte member 111 is formed of, for example, zirconia, and has oxygen-ion conductivity. The electrodes 112 and 113 are provided on opposite surfaces of the solid electrolyte member 111 with respect to the stacking direction of the detection element 10. The electrode 113 is disposed in the first measurement chamber 101 as described above, and the electrode 112 is disposed at a position corresponding to the electrode 113 with the solid electrolyte member 111 intervening between the two electrodes. The electrodes 112 and 113 are formed of a material whose predominant component is Pt. Examples of the material whose predominant component is Pt include Pt, Pt alloy, and cermet containing Pt and ceramic. Notably, an example of the Pt alloy which constitutes the electrodes 112 and 113 is a Pt alloy containing Pt and Au which is low in performance of decomposing $NO_X$. Porous protection layers 114 and 115 formed of a ceramic material are formed on the surfaces of the electrodes 112 and 113, respectively. The electrode 112 of the Ip1 cell 110 is connected to an Ip1+ port of the detection section drive circuit 160 of the sensor control apparatus 190, and the electrode 113 of the Ip1 cell 110 is connected to a COM port (reference potential) of the detection section drive circuit 160.

The Vs cell 120 includes the solid electrolyte member 121, and a pair of porous electrodes 122 and 123. The solid electrolyte member 121 is formed of, for example, zirconia, and has oxygen-ion conductivity. The solid electrolyte member 121 is disposed to face the solid electrolyte member 111 with the insulator 141 intervening therebetween. The electrodes 122 and 123 are provided on opposite surfaces of the solid electrolyte member 121 with respect to the stacking direction of the detection element 10. The electrode 123 is disposed in the reference oxygen chamber 105 as described above, and the electrode 122 is disposed in the first measurement chamber 101 at a position corresponding to the electrode 123, with the solid electrolyte member 121 intervening between the two electrodes. The electrodes 122 and 123 are formed of the above-described material whose predominant component is Pt. The electrode 122 of the Vs cell 120 is connected to the COM port of the detection section drive circuit 160, and the electrode 123 of the Vs cell 120 is connected to a Vs+ port of the detection section drive circuit 160.

The Ip2 cell 130 includes the solid electrolyte member 131, and a pair of porous electrodes 132 and 133. The solid electrolyte member 131 is formed of, for example, zirconia, and has oxygen-ion conductivity. The solid electrolyte member 131 is disposed to face the solid electrolyte member 121 with the insulator 146 intervening therebetween. The electrodes 132 and 133 are provided on the surface of the solid electrolyte member 131 located on the side toward the solid electrolyte member 121 with respect to the stacking direction of the detection element 10. The electrode 133 is disposed in the second measurement chamber 102 as described above, and the electrode 132 is disposed in the reference oxygen chamber 105 such that the solid electrolyte member 131 intervenes between the paired electrodes 132 and 133. The electrodes 132 and 133 are formed of the above-described material whose predominant component is Pt. The electrode 132 of the Ip2 cell 130 is connected to an Ip2+ port of the detection section drive circuit 160, and the electrode 133 of the Ip2 cell 130 is connected to the COM port of the detection section drive circuit 160.

Next, the heater section 15 will be described. The heater section 15 includes insulation layers 152 and 153, and a heater conductor 151. The insulation layers 152 and 153 are formed of a sheet whose predominant component is alumina. The heater conductor 151 is a single, continuous electrode buried between the insulation layers 152 and 153. The heater conductor 151 is formed of a material whose predominant component is Pt, and has a correlation between its temperature and its resistance. One end of the heater conductor 151 is connected to an Htr− port of the heater section drive circuit 170, whereby the one end is grounded. The other end of the heater conductor 151 is connected to an Htr+ port of the heater section drive circuit 170. On the basis of an instruction from the microcomputer 180, the heater section drive circuit 170 controls the duty ratio of an ON/OFF signal supplied to the Htr+ port in accordance with the resistance of the heater conductor 151, whereby the heating temperature of the heater conductor 151 is adjusted.

The reduction section 18, which is a porous body formed of a ceramic material such as alumina, is provided at the front end portion 11 of the detection element 10 having the above-described structure. The reduction section 18 covers the circumference of the front end portion 11 of the detection element 10. The reduction section 18 is disposed on the upstream side of the first diffusion resistor section 103 such that, when the exhaust gas is introduced into the first measurement chamber 101, the exhaust gas passes through the reduction section 18 before passing through the first diffusion resistor section 103. The porosity of the reduction section 18 is higher than that of the first diffusion resistor section 103. A porous body has a large number of continuous pores for allowing gas to pass therethrough, and its porosity is the ratio of the volume of all spaces formed by the pores to the volume of the entire porous body (the volume including the pores). The lower the porosity, the greater the flow resistance acting on gas flowing (passing) through the porous body (the greater the difficulty to pass through the porous body). The first diffusion resistor section 103 is provided so as to produce a flow resistance which limits the introduction speed of the exhaust gas to thereby prevent limitless introduction of the exhaust gas into the first measurement chamber 101. In contrast, the reduction section 18 is provided to serve as a place where, of $NO_X$ contained in the exhaust gas, $NO_2$ undergoes a reduction reaction, as will be described later. Therefore, desirably, the reduction section 18 has a porosity which is higher than that of the first diffusion resistor section 103 and which is determined such that the reduction section 18 does not hinder the flow of the exhaust gas. Notably, the porosity of the reduction section 18 can be rendered higher than that of the first diffusion resistor section 103 by means of adjusting the grain sizes of the material powders of ceramics which constitute intermediates which will become the reduction section 18 and the first diffusion resistor section 103 through firing, or adjusting the amount of a binder contained in the intermediates. Alternatively, in the case where a pore-forming agent which will form pores after firing is contained in the intermediates, the amount of the pore-forming agent is adjusted.

Next, operation of the detection element 10 will be briefly described with reference to FIG. 2. The solid electrolyte members 111, 121, and 131, which constitute the gas detection section 14, are activated by being heated. As described above, the current flowing between the Htr+ port and the Htr− port is controlled by the heater section drive circuit 170, whereby the solid electrolyte members 111, 121, and 131 are quickly activated. After completion of activation, the heating temperature of the heater conductor 151 is maintained at a predetermined temperature (e.g., 750° C.). Since the entirety of the front end portion 11 of the detection element 10 is heated when the heater conductor 151 heats the solid electrolyte members 111, 121, and 131, the reduction section 18 provided at the front end portion 11 is also heated.

When the exhaust gas flowing through the exhaust pipe is introduced into the protector 8 (see FIG. 1) of the $NO_X$ sensor 1, the exhaust gas passes through the reduction section 18, and is introduced into the first measurement chamber 101 through the first diffusion resistor section 103. The $NO_X$ contained in the exhaust gas includes NO and $NO_2$. When the exhaust gas passes through the reduction section 18, the exhaust gas is heated by the reduction section 18 to at least a reduction temperature (e.g., 650° C.) required for reduction of $NO_2$ to NO. As a result, most of the $NO_2$ contained in the exhaust gas is reduced to NO, and, when the exhaust gas passes through the first diffusion resistor section 103, most of the $NO_X$ contained in the exhaust gas is NO(NO contained in the exhaust gas from the beginning, and NO reduced from $NO_2$).

On the basis of an instruction from the microcomputer 180, the detection section drive circuit 160 applies a predetermined voltage to the Vs+ port. As a result, the Vs cell 120 pumps oxygen out of the reference oxygen chamber 105 or pumps oxygen into the reference oxygen chamber 105 (performs so-called oxygen pumping) such that the oxygen partial pressure within the reference oxygen chamber 105 becomes a predetermined level. When the oxygen partial pressure within the exhaust gas introduced into the first measurement chamber 101 differs from the oxygen partial pressure within the reference oxygen chamber 105, oxygen ions move between the first measurement chamber 101 and the reference oxygen chamber 105 via the Vs cell 120 such that the two oxygen partial pressures are balanced, whereby an electromotive force is generated between the electrodes 122 and 123.

The detection section drive circuit 160 controls the current supplied to the Ip1+ port such that the voltage at the Vs+ port becomes the above-described predetermined voltage (e.g., 425 mV). As a result of this control, pumping out and pumping in of oxygen is performed between the atmosphere within the first measurement chamber 101 to which the electrode 113 is exposed and the outside atmosphere to which the electrode 112 of the detection element 10 is exposed. Thus, the concentration of oxygen contained in the exhaust gas is adjusted to a predetermined low level.

The exhaust gas having an adjusted oxygen concentration is introduced into the second measurement chamber 102 through the second diffusion resistor section 104. Within the second measurement chamber 102, NO contained in the exhaust gas is decomposed by means of the catalytic action of the electrode 133 whose predominant component is Pt, whereby $NO_X$-originating oxygen (oxygen originating from NO contained in the exhaust gas from the beginning and oxygen originating from NO reduced from $NO_2$) is generated. The $NO_X$-originating oxygen flows through the Ip2 cell 130 in the form of oxygen ions. As a result, a current flows through the Ip2 cell 130, whereby an output corresponding to the concentration of $NO_X$ contained in the exhaust gas can be obtained from the Ip2+ port.

As described above, in the $NO_X$ sensor 1 of the present embodiment, through provision of the reduction section 18 upstream of the first diffusion resistor section 103 of the detection element 10, $NO_2$ contained in the exhaust gas can be caused to pass through the first diffusion resistor section 103 after being reduced to NO. When $NO_X$ passes through the first diffusion resistor section 103, $NO_2$, which is greater in molecular weight than NO, is lower in the degree of diffusion (lower in passing speed) as compared with NO. Since $NO_2$ is reduced to NO at the reduction section 18, the exhaust gas passing through the first diffusion resistor section 103 hardly contains $NO_2$. Therefore, the passage (flow) of $NO_X$ through the first diffusion resistor section 103 is not limited by $NO_2$. Accordingly, the detection element 10 of the present embodiment can have an improved sensitivity for detection of $NO_X$ because of provision of the reduction section 18. Although it is desired that all the $NO_2$ contained in the exhaust gas is reduced to NO at the reduction section 18, even in the case where a portion of the $NO_2$ remains without being reduced to NO, the $NO_X$ detection sensitivity can be improved so long as the amount of $NO_2$, which limits the speed at which $NO_X$ passes through the first diffusion resistor section 103, can be reduced.

Also, since $NO_2$ is reduced to NO at the reduction section 18, $NO_2$ is not required to be reduced to NO within the first measurement chamber 101. Moreover, since the porosity of the reduction section 18 is higher than that of the first diffusion resistor section 103, the flow resistance at the reduction section 18 hardly hinders passage of the exhaust gas therethrough. Therefore, because of provision of the reduction section 18, the detection element 10 of the present embodiment can have a higher sensitivity for detection of $NO_X$.

This reduction section 18 is heated, together with the solid electrolyte members 111, 121, and 131, as a result of heat generation of the heater conductor 151 of the heater section 15. When the exhaust gas passes through the heated reduction section 18, $NO_2$ is heated to a predetermined reduction temperature or higher, and is reduced to NO. A reduction temperature of 650° C. or higher is preferred because $NO_2$ can be completely reduced to NO. Needless to say, a reduction temperature lower than 650° C. may be employed so long as the reduction temperature is sufficient for reduction of $NO_2$ to NO at the reduction section 18.

Notably, the present invention is not limited to the above-described embodiment, and may be modified in various manners. Using a porous body as the reduction section 18 is preferred from the viewpoint of heating the exhaust gas passing through the reduction section 18 for efficient reduction of $NO_2$ contained in the exhaust gas to NO. However, the reduction section 18 is not necessarily required to be a porous body so long as the reduction section 18 has a structure which enables heating of the exhaust gas to the reduction temperature or higher. For example, a passage may be provided on the upstream side of the first diffusion resistor section 103 so that the exhaust gas passing through that passage is introduced to the first measurement chamber 101 via the first diffusion resistor section 103 after being heated to the reduction temperature or higher (after $NO_2$ is reduced to NO). Also, in the above-described embodiment, the reduction section 18 is provided to cover the front end portion 11 of the detection element 10; however, the reduction section 18 is not necessarily required to cover the front end portion 11, so long as the reduction section 18 is disposed on the upstream side of the first diffusion resistor section 103.

In the above-described embodiment, the reduction section 18 is heated by the heater section 15 provided for heating the solid electrolyte members 111, 121, and 131. However, a heater for heating the reduction section 18 may be provided separately from the heater section 15. In the case where a heater for heating the reduction section 18 is provided separately, the reduction section can be heated without being affected by the mounting position of the $NO_X$ Sensor and its element structure.

The reduction section 18 may bear a reduction catalyst, such as Pt or Rh, which catalyzes the reduction reaction of $NO_2$ to NO. When the reaction is accelerated by the reduction catalyst, the reduction of $NO_2$ to NO at the reduction section can be performed more reliably, whereby the sensitivity of the $NO_X$ sensor 1 can be enhanced further. Notably, when the reduction section 18 bears the above-mentioned reduction catalyst, the heating temperature of the reduction section 18 can be set to a rather low temperature. Also, the reduction section 18 may function as a protection layer for protecting the detection element 10, which is exposed to exhaust gas, from being poisoned.

Notably, in the present invention, the first diffusion resistor section 103 corresponds to the "diffusion resistor section." The solid electrolyte member 111 and the electrodes 112, 113 correspond to the "first solid electrolyte layer" and the "pair of first electrodes," respectively, and the solid electrolyte member 131 and the electrodes 132, 133 correspond to the "second solid electrolyte layer" and the "pair of second electrodes," respectively. The heater conductor 151 corresponds to the "heater."

DESCRIPTION OF REFERENCE NUMERALS

1: $NO_X$ sensor
18: reduction section
101: first measurement chamber
102: second measurement chamber
103: first diffusion resistor section
110: Ip1 cell
111: solid electrolyte member
112: electrode
113: electrode
130: Ip2 cell
131: solid electrolyte member
132: electrode
133: electrode
151: heater conductor

The invention claimed is:

1. A gas sensor for detecting concentration of $NO_x$ contained in an object gas, comprising:
a first measurement chamber into which the object gas is introduced via a diffusion resistor section which limits flow of the object gas therethrough;
a reduction section provided outside of the first measurement chamber and upstream of the diffusion resistor section, wherein the reduction section reduces $NO_2$ contained in the object gas introduced into the first measurement chamber to NO;
a first oxygen pump cell having a first solid electrolyte layer and a pair of first electrodes provided on the inner and outer sides of the first measurement chamber;
a second measurement chamber which is located downstream of the first measurement chamber and into which the object gas is introduced from the first measurement chamber; and
a second oxygen pump cell having a second solid electrolyte layer and a pair of second electrodes provided on the inner and outer sides of the second measurement chamber, wherein a current corresponding to the amount of oxygen produced as a result of decomposition of NO contained in the object gas introduced into the second measurement chamber flows between the pair of second electrodes; wherein
each of the diffusion resistor section and the reduction section is formed of a porous body having a large number of continuous pores through which the object gas flows; and
the reduction section has a porosity higher than that of the diffusion resistor section.

2. A gas sensor according to claim 1, further comprising a heater for heating the reduction section, wherein, as a result of heating by the heater, the reduction section heats the object gas flowing through the reduction section to at least a reduction temperature required for reduction of $NO_2$ to NO.

3. A gas sensor according to claim 1, wherein the reduction section bears a reduction catalyst which catalyzes a reduction reaction of $NO_2$ to NO.

* * * * *